United States Patent [19]
Cho et al.

[11] Patent Number: 5,083,549
[45] Date of Patent: Jan. 28, 1992

[54] ENDOSCOPE WITH TAPERED SHAFT

[75] Inventors: George E. Cho, Sudbury; Horace Furumoto, Wellesley, both of Mass.

[73] Assignee: Candela Laser Corporation, Wayland, Mass.

[21] Appl. No.: 557,958

[22] Filed: Jul. 25, 1990

Related U.S. Application Data

[63] Continuation-in-part of Ser. No. 307,321, Feb. 6, 1989, abandoned.

[51] Int. Cl.$^5$ .............................................. A61B 1/06
[52] U.S. Cl. ........................................... 128/7; 128/4; 604/21; 604/22; 604/28
[58] Field of Search .................. 128/7; 604/21, 22, 28

[56] References Cited

U.S. PATENT DOCUMENTS

| | | | |
|---|---|---|---|
| 1,995,196 | 3/1935 | Wolf | 128/7 |
| 3,788,304 | 1/1974 | Takahashi | 128/6 |
| 4,146,019 | 3/1979 | Bass et al. | 128/6 |
| 4,483,326 | 11/1984 | Yamaka et al. | 128/4 |
| 4,589,404 | 5/1986 | Barath et al. | 128/6 |
| 4,685,449 | 8/1987 | Bonnet | 128/4 |
| 4,690,175 | 9/1987 | Ouchi et al. | 128/4 X |
| 4,802,461 | 2/1989 | Cho | 128/7 |
| 5,031,603 | 7/1991 | Gautier et al. | 128/4 |

FOREIGN PATENT DOCUMENTS

WO86/06642 11/1986 PCT Int'l Appl. .

OTHER PUBLICATIONS

Richard Wolf Medical Instruments Catalog, III 87, 1987, pp. D1-D43, D58-D60; FOL-5.

W. B. Allan, "Fiber Optics Theory and Practice," *Optical Physic and Engineering*, Series Editor William L. Wolfe, Plenus Press, 1973, pp. 148-176.

Denise Grady, "The Artery Zapper," *Discover*, Dec. 1982, pp. 36-40.

Yoshikatsu Tanahashi, M. D., "Transurethral Disintegration of Urinary Calculi by the Use of Laser Beam", *Urology*, vol. 10, pp. 30-33, 1981.

*Primary Examiner*—William H. Grieb
*Attorney, Agent, or Firm*—Hamilton, Brook, Smith & Reynolds

[57] ABSTRACT

A fiber optic endoscope has a shaft with a varying outer diameter. The distal end of the shaft is sufficiently small in outside diameter for maneuvering it through various body canals, and is useful in dilating body orifices to allow more proximal, longer-diameter portions of the shaft to penetrate. The endoscope shaft changes in thickness and is preferably in stages of different constant outside diameter. A flexible tip portion at the distal end of the shaft which is controllable from the endoscope handle may be included. Transitions between adjacent stages are smooth to provide a gradual transition between stages. The endoscope outer shaft is preferably made from a one-piece structure, portions of which are reduced in outside diamter to provide the different stages of the endoscope shaft.

25 Claims, 6 Drawing Sheets

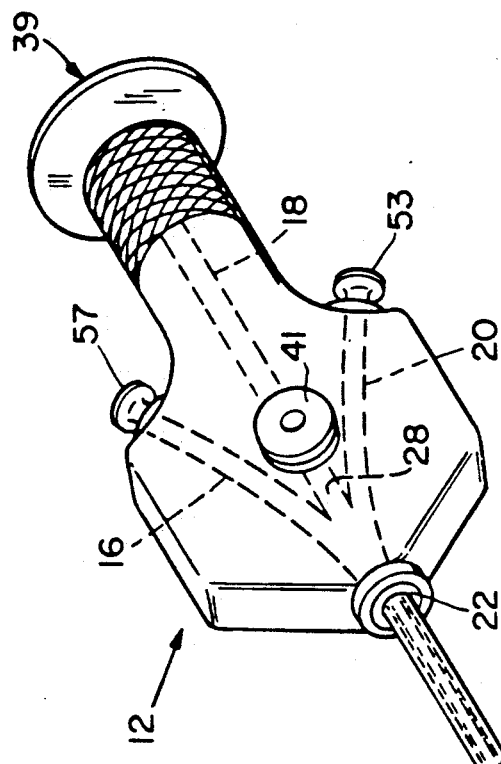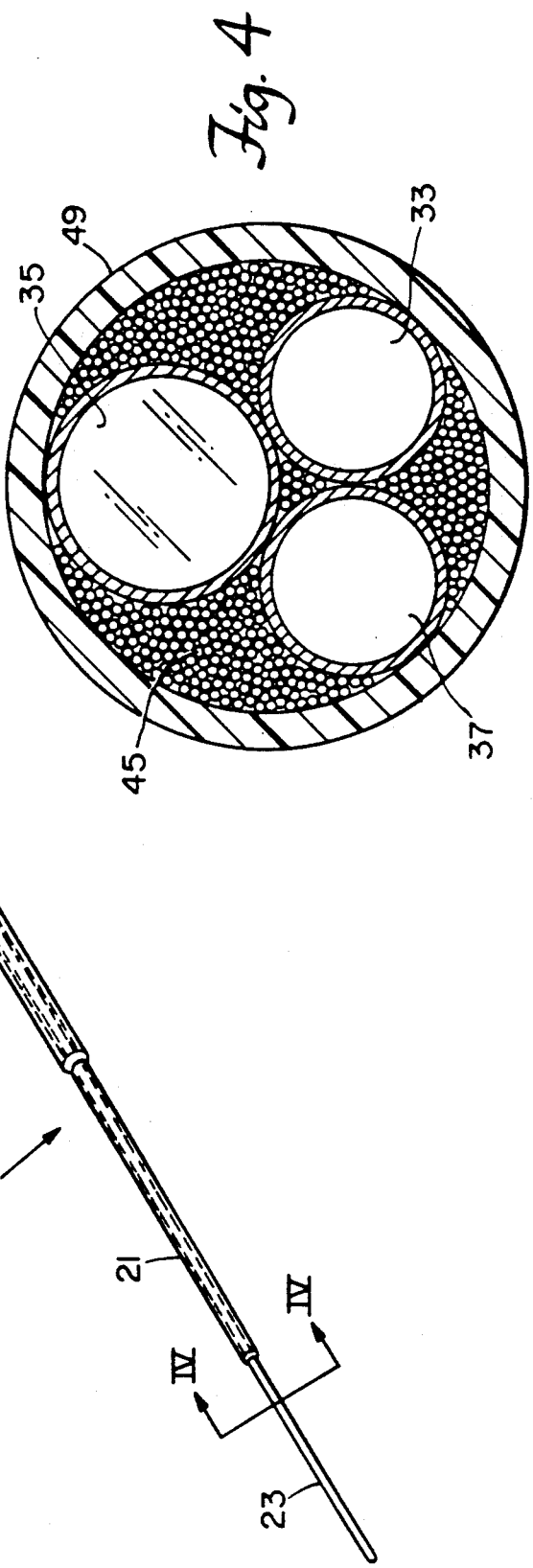

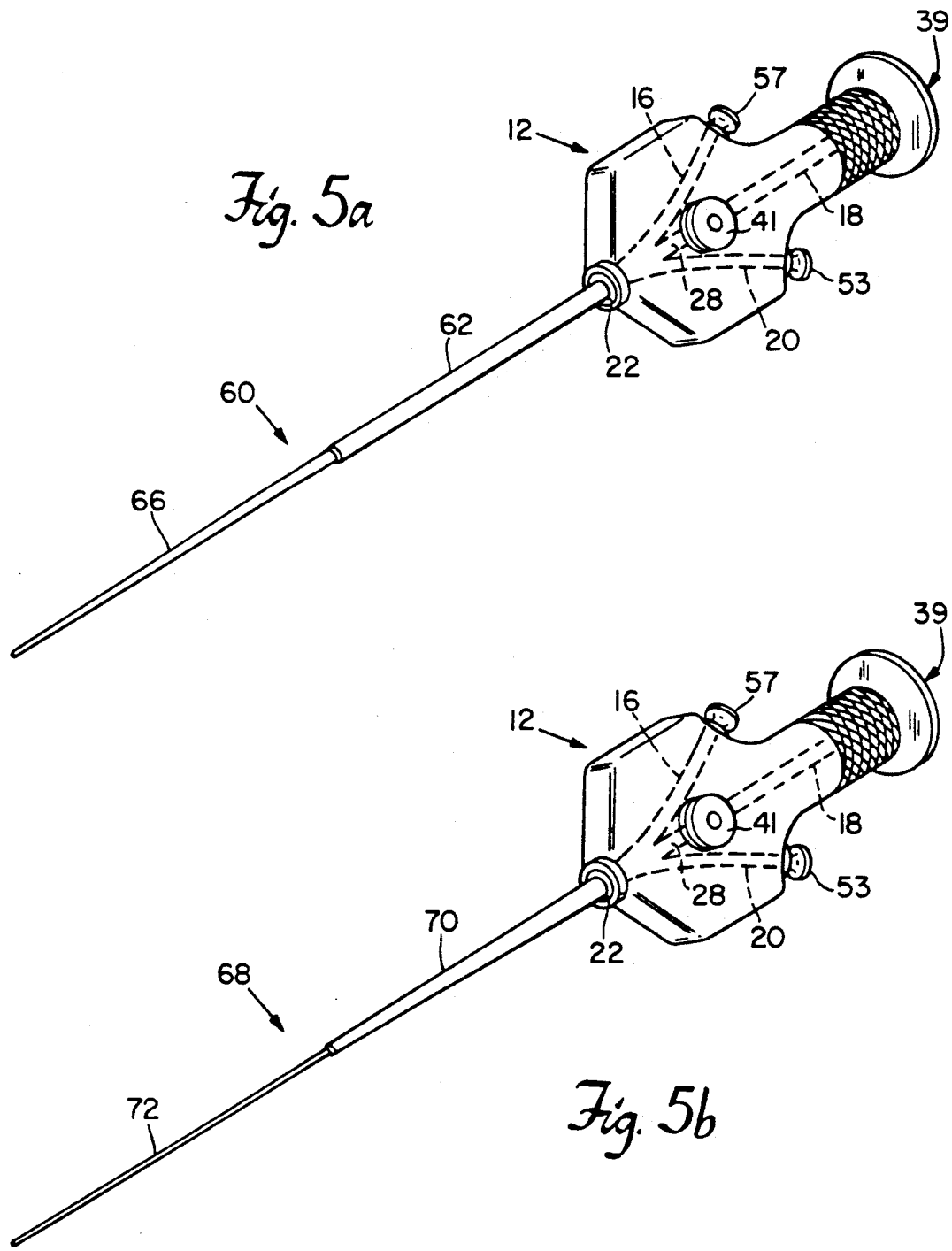

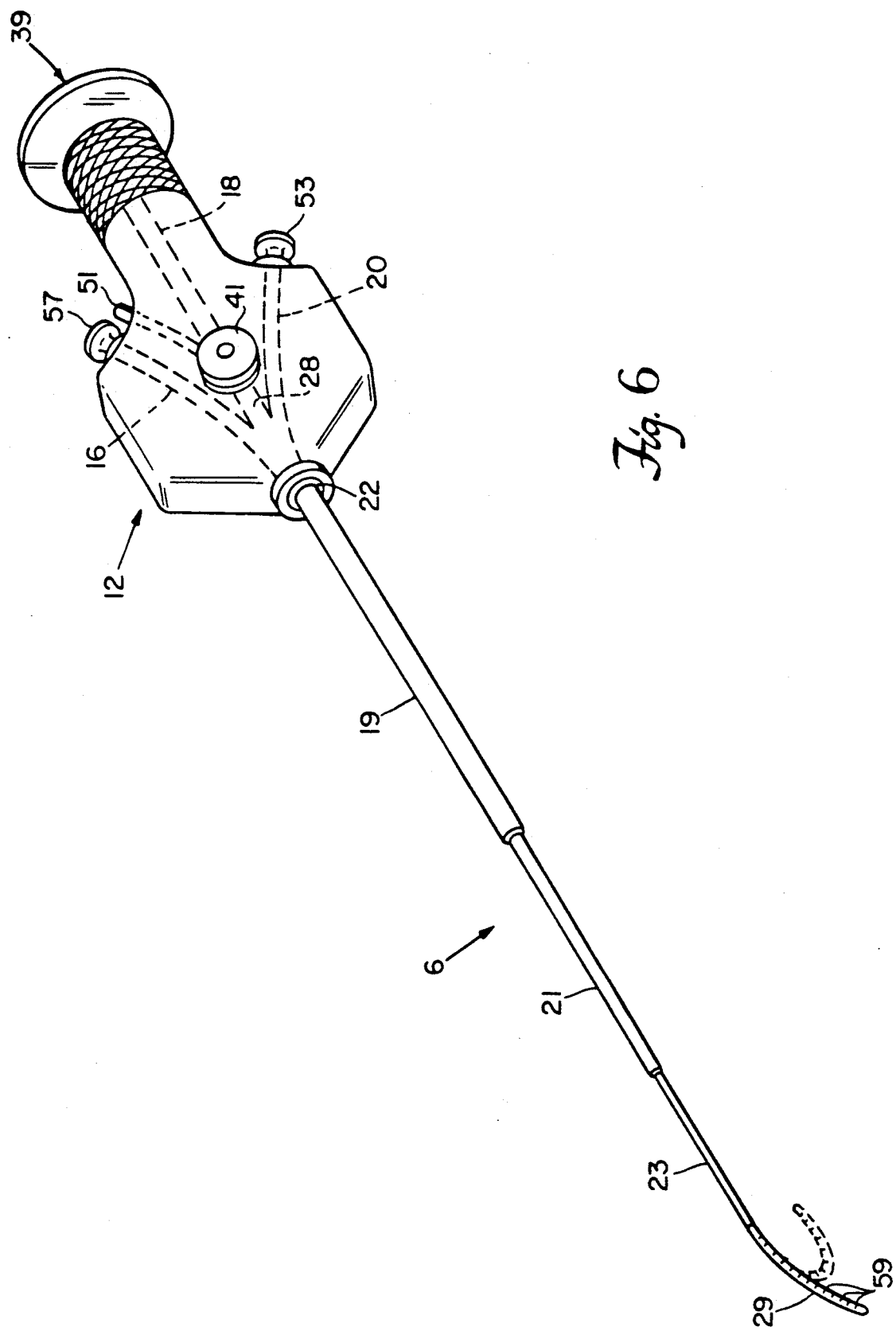

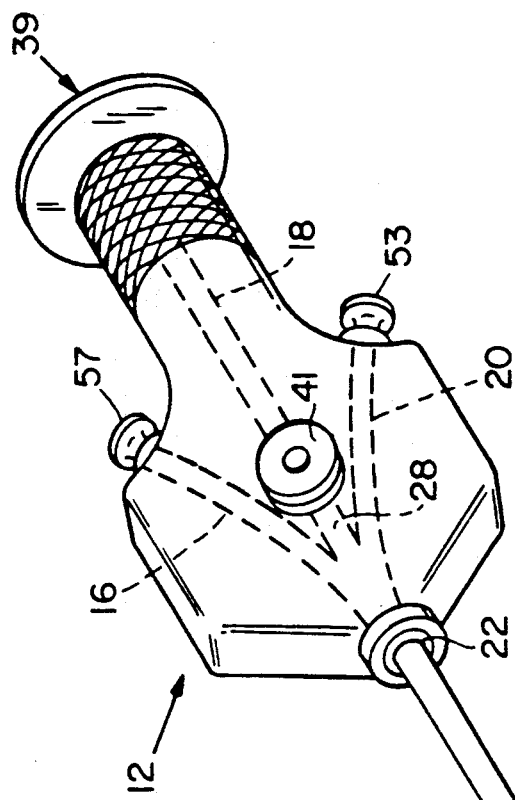
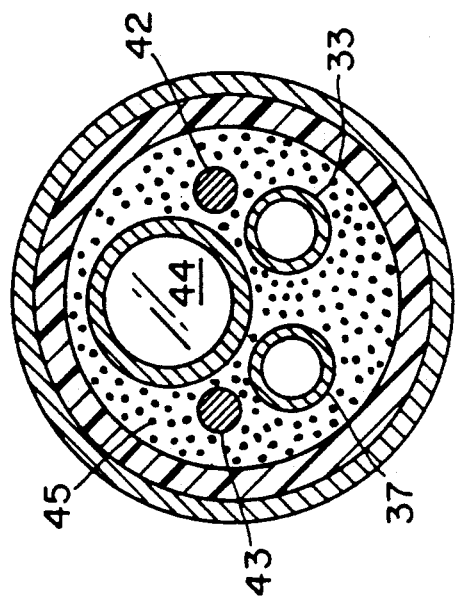

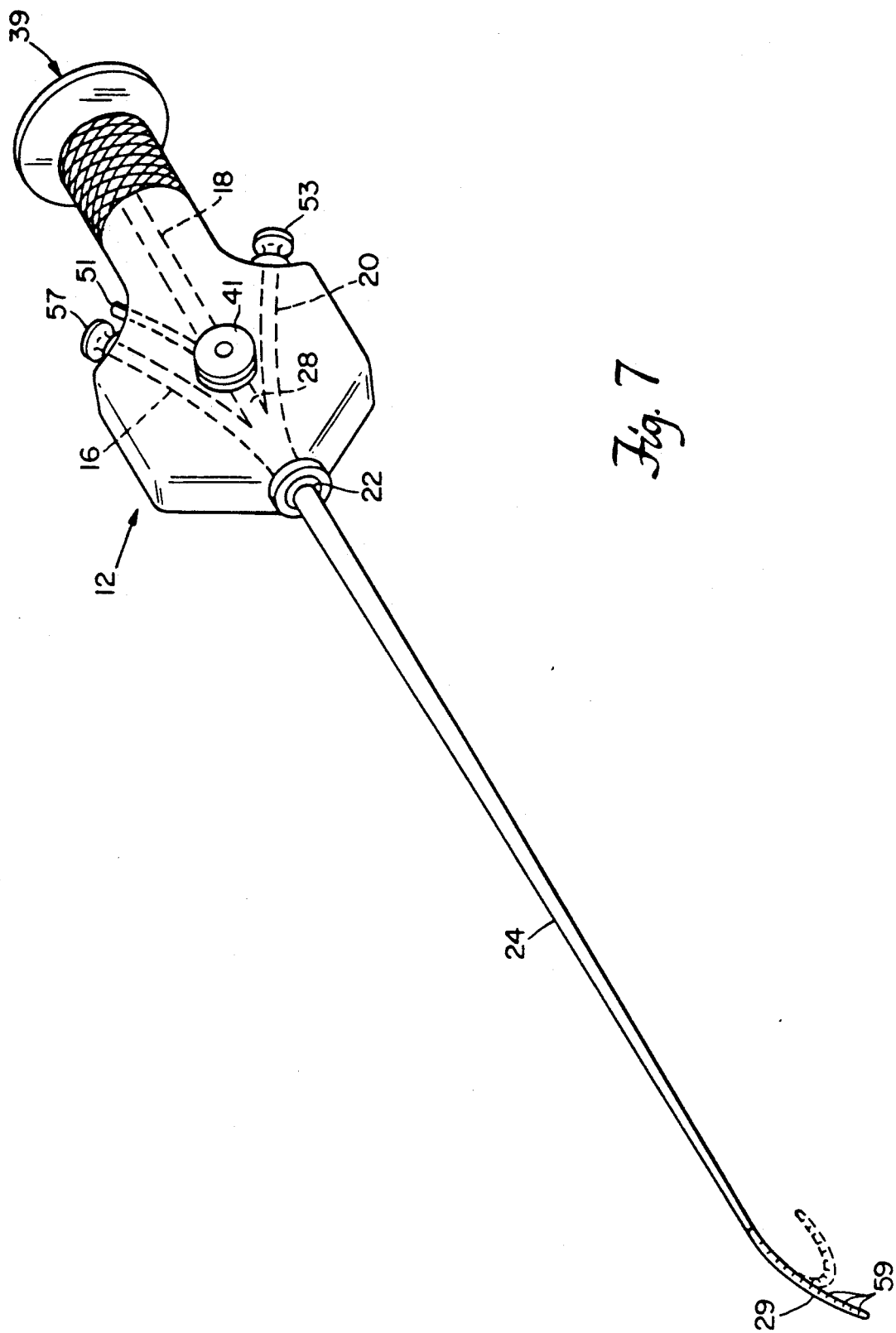

ENDOSCOPE WITH TAPERED SHAFT

This is a Continuation-in-Part of Application Ser. No. 07/307,321 "Endoscope With Tapered Shaft", filed Feb. 6, 1989, now abandoned.

BACKGROUND OF THE INVENTION

The invention disclosed herein pertains to an endoscope used to visualize the urinary system. As shown in FIG. 1, kidneys 13 of the human body are connected to a bladder 9 by very narrow ducts called ureters 11. The openings of the ureters 11 into urinary bladder 9 are about 1 to 4 mm wide. Bladder 9 is partially surrounded from behind by pelvis 15 which serves as a protective shield for the bladder. The natural flow of body fluids is from the kidneys 13 through ureters 11 into bladder area 9 and is discharged from the body through urethra 17. The opening of the urethra to release fluids from the body is about 5 mm to 10 mm wide.

Urinary bladder stones 8 and kidney stones 7 have been known to become lodged in the bladder 9 and ureters 11, as well as in the calyxes 5 of the kidney 13, respectively. This causes blockage of flowing body fluids and is very painful. Various medical devices have been developed to remove bladder stones 8, and/or kidney stones 7. The devices for removing these stones are pertinent to the general subject matter of the present invention.

The medical devices which have been developed to remove kidney stones generally involve a device called a ureteroscope. The ureteroscope is positioned within the body (i.e. urethra 17, bladder 9 and ureter 11) and has working channels which provide access to and from the areas where stones 7, 8 are lodged. A typical ureteroscope is rigid along its length so as to enable axial and rotational translation in the bladder 9 areas. Typically, the rigid ureteroscope is greater than 3 mm in diameter and therefore unable to fit through most openings into ureters 11 in their natural size. Ureters 11 can be mechanically dilated by separate accessory means to accommodate the ureteroscope. This dilation, however, is traumatic to the body. Even after entering the ureter 11, and subsequently the kidneys 13, the rigid ureteroscope is unable to bend toward kidney stones 7 lodged in calyxes 5 of kidneys 13.

Flexible ureteroscopes have been developed to serve the same purpose as the rigid ureteroscopes. Typically, these ureteroscopes tend to be too flexible to allow adequate control when adjusted from a handle at a proximal end. Proper manual control requires a more rigid length for the endoscope to be effectively moved along the urinary tract.

A rigid endoscope with a flexible tip is disclosed in U.S. Pat. Application Ser. No. 089,579, assigned to the assignee of the present invention. The rigid length of the endoscope has an outer diameter of 3 mm or less, and includes a flexible tip portion at the distal end which is controllable from the endoscope handle. The flexible tip portion is designed to fit easily into a desired ureter, and thereafter bend toward kidney stones 7 in calyxes 5.

Employed within a working channel of a ureteroscope are various mechanical accessories for engulfing and retrieving, or grasping and crushing kidney stones 7. Also, a rigid ultrasound probe for delivering ultrasound waves to break the kidney stones 7 has been developed to be employed in a working channel of a rigid ureteroscope. Further, an electrohydraulic generator has been developed to generate a spark at the tip of a probe to break target kidney stones 7 which are located with the ureteroscope.

Recently, "extracorporeal acoustic shock wave" therapy has been used to break kidney stones into particles which are small enough to pass through the ureter and urethra by natural means. This therapy involves immersing the patient in a bath of water or placing the body of the patient in contact with a water column enclosing a shock wave generator. Shock waves are generated in the water and focused toward the areas where target kidney stones are lodged. The waves penetrate the body from the outside and break the target stones. However, such acoustic shock wave therapy or treatment may not affect kidney stones which are lodged in the lower region of ureters 11 and protected by the surrounding pelvis 15.

More recently, the Candela Laser Corporation, Wayland, Mass., has developed a dye laser to apply a photoacoustic effect to kidney stones 7 which are lodged in areas protected by the pelvis 15 and in other areas. Such an effect breaks the stones into particles which are small enough to pass through the ureter and urethra.

SUMMARY OF THE INVENTION

The present invention provides an endoscope which minimizes trauma associated with entrance into a ureter as generated by existing devices. The endoscope employs a main outer shaft which is preferably one-piece and which has an outside diameter that varies along its length and in particular decreases toward the distal end, either uniformly or in overlapping stages. The shaft has a circular cross section in a preferred embodiment. By having a thin distal end, the endoscope has a leading tip which is small enough to enter tight body canals. By being wider at the proximal end, the endoscope is sufficiently rigid to enable rotational and translational control from the proximal end. The rigidity of the endoscope shaft is such that when supported by the handle, a minimum force of 250 gm applied in a normal direction at the distal end of the shaft causes the distal end to undergo a deflection of about 5 cm.

The varying outer diameter of the endoscope provides an added feature of incidentally dilating canals into which the endoscope is inserted. The thin distal end penetrates and dilates subject body canals to a degree which allows the wider portions of the device to easily follow. Such dilation is gradual and hence less traumatic than with existing devices.

The thickness between an inside diameter and an outside diameter of the endoscope shaft varies along the length of the shaft. In a preferred embodiment the shaft has a substantially constant inside diameter, and the finished outside diameter at the distal end of the shaft is less than 3 mm. The outside diameter increases from the distal end toward the proximal end in steps of constant outside diameter. A transition between the distal-most stage and an adjacent stage is in the distal third of the shaft. An increase in outside diameter of at least 20% exists between each stage and any adjoining stage toward the proximal end.

The endoscope may be multi-channeled, the different channels being contained within the endoscope shaft. One channel is for viewing through from the handle end of the shaft to subjects outside the distal portion of the shaft. A second channel is for carrying optical fiber to the distal end of the shaft for delivering laser radiation to the subject stones adjacent to and outside the distal end of the shaft. Another channel might be used to house fiber for carrying illuminating light from a light source at the proximal end to the region outside the distal end. A channel might also be used to pass fluids to and from the ureter and bladder area.

To avoid tearing tissue around the area being examined, the distal end of the endoscope can be filled with an epoxy and ground to a smooth curved radius. This further prevents or limits inducing trauma in the subject.

Different embodiments of the present invention involve the way in which the outer diameter of the endoscope varies along its length. In the embodiment in which the endoscope shaft is formed by a series of stages, the transition between each stage is smoothed to prevent the exposure of sharp edges. A preferred method of fabricating this stepped endoscope is by forming a cylindrical shaft with a diameter of the thickest step desired, and machining the shaft to reduce the diameter in regions where thinner steps are desired.

The endoscope shaft may include a flexible tip at the distal end. This tip houses the working channels of the endoscope and is guided by the shaft. The tip portion can be maneuvered laterally relative to the length of the shaft under user control. A set of wires connected to the tip portion leading through the shaft to the handle provides the means for control.

In accordance with the foregone, the present invention may be used for examining a subject's body canals. The small diameter distal end of the endoscope dilates any tight openings upon insertion of the device therein. This then allows the larger diameter portions of the endoscope to fit within these openings. Thereafter the endoscope is easily maneuvered by the proximal end and enables the distal end of the endoscope to be positioned adjacent to a stone in question for viewing and/or treatment. If a channel for transferring laser radiation is also included, laser energy is transmitted to the stone, breaking it into pieces small enough to pass through the subject's urinary tract.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 2 is a schematic view of a step-tapered endoscope embodying the present invention.

FIG. 3 is a schematic view of a uniformly tapered endoscope embodying the present invention.

FIG. 4 is a cross section of the endoscopes of FIGS. 2 and 3 through line IV—IV.

FIGS. 5a and 5b show alternative shaft designs utilizing the step-tapered and uniformly tapered shaft design concepts.

FIG. 6 is a schematic view of an step-tapered endoscope with a tapered tip embodying the present invention.

FIG. 7 is a schematic view of a uniformly tapered endoscope with a flexible tip embodying the present invention.

FIG. 8 is a cross section of the flexible tip of FIGS. 6 and 7.

DETAILED DESCRIPTION OF THE PREFERRED EMBODIMENTS

Figure 1:
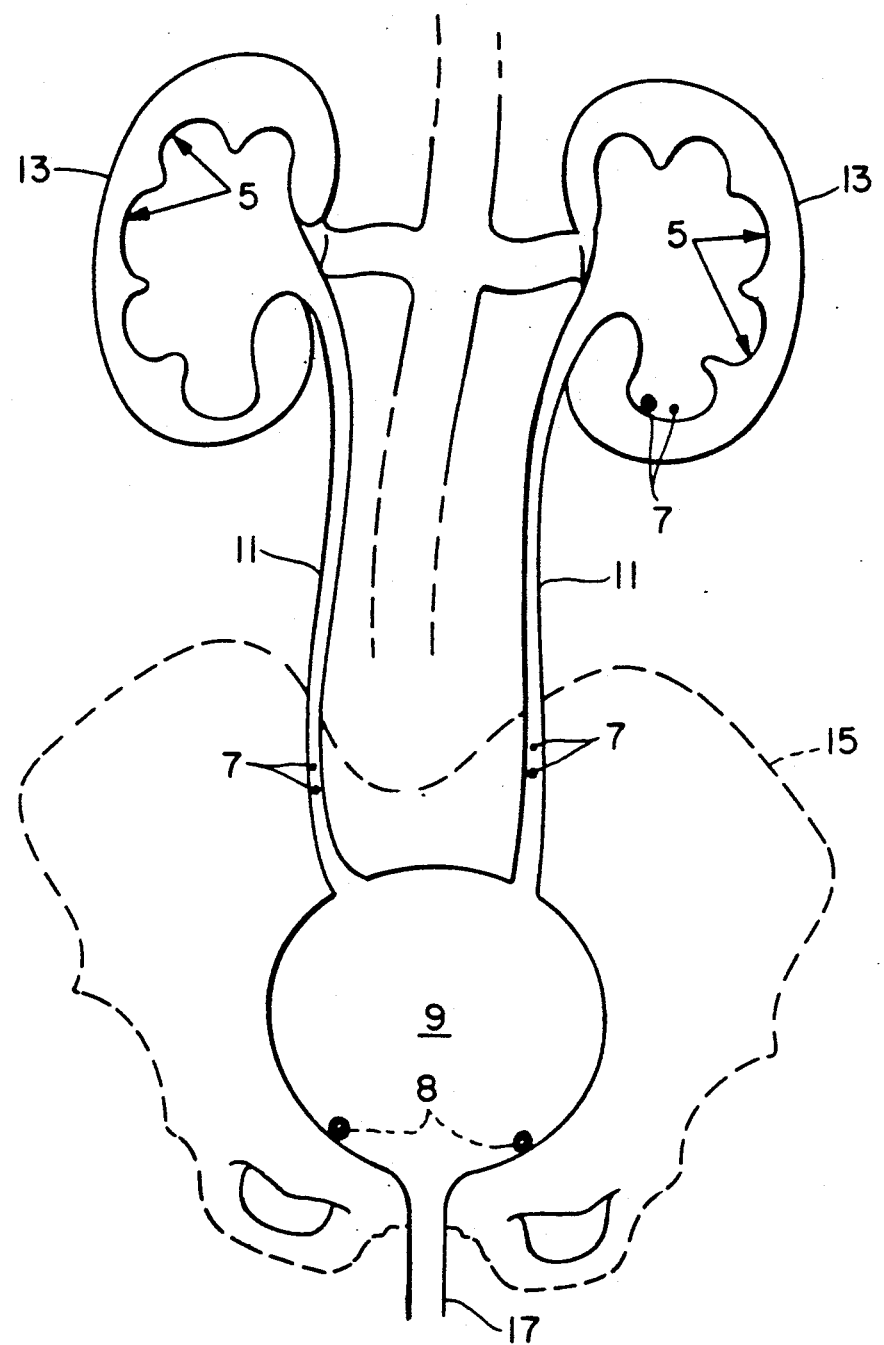
FIG. 1 is a schematic view of the bladder area of a human body.

An endoscope embodying the present invention is provided in FIG. 2. The endoscope has a handle 12 connected to a hollow main outer shaft 6 with three stages 19, 21, 23 of different outside diameter, the stage 23 with the smallest outside diameter being toward the distal end of the endoscope. The handle 12 has numerous bores 16, 18, 20 which converge at a common aperture 22 and are coupled to respective working channels that run the length of major shaft 6. Each bore 16, 18, 20 opens on a different side of the handle 12.

The overall length of the shaft is about 37–44 cm. The distal stage 23 of the endoscope shaft is preferably about 5–12 cm long with an outer diameter of about 2.4 mm. The middle stage 21 is preferably 10–13 cm long with an outside diameter of about 3 mm. The proximal stage 19 is preferably about 20–23 cm long with an outer diameter of about 3.8 mm. With the above dimensional ranges, the step between the distal-most and middle stages is in the distal third of the shaft. Furthermore, the change in outside diameter from the distal-most stage and the middle stage is about 25% and the change in outside diameter from the middle stage to the proximal stage is about 27%. The rigidity of the endoscope main shaft 6 is such that when supported by the handle 12, the distal end will undergo a deflection of 5 cm when a minimum force of 250 grams is applied to the distal end in a direction normal to the endoscope shaft 6.

One variation of this embodiment is a pediatric version of the same endoscope. Because a child's muscle tissue is not as tough as an adults, the endoscope can be less rigid and the distal stage longer. Referring to FIG. 2, the distal stage 23 of the pediatric version of this endoscope is preferably about 12–13 cm long, the middle stage 21 is about 5 cm long, and the proximal stage about 5 cm long. The outer diameters of the stages 19, 21, 23 are about the same as in the adult version.

The intended usage of this embodiment is for the internal examination of a subjects urinary tract. The diameter of the distal stage 23 of the endoscope is small enough to easily and atraumatically enter the opening from the bladder 9 (FIG. 1) to the ureter 11 on most subjects. Once within the ureter 11, the distal stage 23 of the endoscope dilates the opening wide enough for the middle stage 21 to enter substantially trouble free. Thereafter further examination into the ureter 11 is enabled by the other features of the endoscope as described later.

The larger diameters of the middle and proximal stages 21, 19 make it difficult for these stages to penetrate small openings, but the increased rigidity they provide allows the endoscope to be fully controlled from the handle. This embodiment provides sufficient rigidity at the distal end 23 for maneuvering the handle 12 to get the shaft through the body canals of the subject without uncontrolled bending of the shaft in the open region of the bladder 9. Hence, the user is able to insert the endoscope into the urethra area 17 and maneuver the endoscope through the bladder area 9 in such a way that the distal end 23 easily reaches and enters the opening of the ureter 11.

Using one fabrication method, each stage of the endoscope shaft is formed by an individual tube of different outer diameter than the tubes forming the other stages. Each tube runs from the handle 12 toward the distal end of the endoscope along a common axis. The smallest diameter tube extends further than the next smallest diameter tube which extends further than the largest diameter tube. This partial overlapping of coaxial tubes forms the three stages 19, 21, 23. Solder is applied to the exposed ends of the two larger diameter tubes to round the ends and provide a smooth, rounded transition where a sharp edge might otherwise be. At the distal end of the endoscope, the tip of the smallest tube is filled with epoxy and ground to form a rounded tip. The tip is polished smooth so it does not scratch the subject. All of the working channels are contained within the smallest diameter tube. The larger diameter tubes provide increased rigidity for the overall length of the endoscope. By providing at least three stages, the stress at each transition with bending is reduced relative to the stress which would result in a two-stage device.

An alternative method of fabricating a step-tapered endoscope shaft involves the machining of a cylindrical tube. The cylinder is chosen to have the same outside diameter as stage 19, and the same inside diameter as stage 23. The different stages are then formed by machining the outside of the cylindrical shaft to reduce the outside diameter in particular regions of interest, thus forming the thinner stages. The shaft therefore has a constant inside diameter and a varying outside diameter which is concentric with the inside diameter. Thus the thickness of the tube, being the difference between the inside diameter and the outside diameter, varies along the length of the shaft along with the outside diameter. Since the shaft is machined from a cylindrical tube, the final step-tapered shaft is a one-piece structure.

In another embodiment of the present invention, the shaft of an endoscope is tapered uniformly along its entire length as shown in FIG. 3. The outer diameter of the shaft 24 of this embodiment changes uniformly from about 2.4 mm at the distal end to about 3.8 mm at the proximal end. This embodiment provides a rigidity similar to the previous embodiment, without the shaft being in different individual stages. This allows the gradual dilation of any tight openings with the slow advance of the endoscope therethrough and more uniform distribution of stress with bending.

The overall length of the shaft 24 in this embodiment is about 40 cm, and it is designed to have the same measure of flexibility as the step-tapered embodiment illustrated in FIG. 2. The inner diameter of the shaft 24 is uniform along the length of the shaft, and all the working channels of the endoscope are contained within that region. As with the step-tapered version, the distal tip of the endoscope is filled with epoxy and ground smooth to avoid sharp edges.

FIGS. 5a and 5b show two possible combinations of the step-tapered and the uniformly tapered design concepts. In FIG. 5a, the shaft 60 has a proximal step portion 62 of constant outside diameter, connected to a uniformly tapered distal portion 66. FIG. 5b shows a shaft 68 with a uniformly tapered proximal end 70 connected to a distal stage 72 of constant outer diameter. It is apparent that a number of different combinations of shaft portions are possible, and the preferred embodiments described are for illustration only. The spirit and scope of the invention is not limited to these examples.

For each of the described embodiments, the endoscope is multi-channeled as shown in the cross section of FIG. 4. The handle 12 is the same for each of the embodiments and the bores in handle 12 lead to respective channels of the endoscope shaft continuing to the distal end of the endoscope.

Bore openings 53, 57 shown in FIG. 2 on different sides of handle 12 lead to working channels 33 and 37, respectively, of FIG. 4. One working channel 33 (37) is used to carry laser radiation. In a preferred embodiment, an optical fiber from a Candela Laser Corp. tuneable dye laser is inserted through bore opening 53 (57) into working channel 33 (37). When the distal end of the endoscope is positioned adjacent to a target calculus such as a stone 7, the laser is activated and laser radiation is transferred through the working channel to the stone. The other working channel 37 (33) carries fluids to and from the body.

Bore opening 39 leads to image carrying channel 35 of FIG. 4 through which the body canals and target stones 7 are viewed. That is, the user looks through bore opening 39, while maneuvering endoscope shaft 6, 24 within the body by handle 12, to view his way through the pertinent body canals (i.e., urethra, bladder area, ureter, and kidney) and to locate target stones 7. A view of the respective area is conveyed through coherent fiber optics in image channel 35 from the distal end to the handle 12 and out bore opening 39.

To aid in viewing, light is provided through the endoscope by fiber optics or other light sources. Fiber optics 45 may be inserted into bore 28 (FIG. 2) through bore opening 41 in handle 12 which leads to areas between the working channels of the endoscope. The fiber optics, typically non-coherent, reach the distal end and provide enough light to enable a clear view of the subject area. Alternatively, fiber optics may be positioned within image channel 35.

The channels 33 and 37 are preferably cylindrical, plastic or non-metallic tubings, each with an outer diameter of about 0.7 mm. The image channel 35 is enclosed by a tube with an outer diameter of about 1 mm. The tube may be stainless steel or some other protective material. An outer casing 49, another cylindrical tubing preferably of stainless steel, encloses the working channels and the fiber optics.

A variation of any of the described embodiments is the addition of a flexible tip portion 29 extending from the distal end of the endoscope shaft. FIG. 6 shows the step-tapered shaft 6 with a flexible tip portion 29, and FIG. 7 shows the uniformly tapered shaft 24 with a flexible tip portion 29. In both cases, the flexible tip 29 is user deflectable by controls in the handle 12 to be described. The other possible shaft embodiments may use the flexible tip but are not shown. Preferably the flexible tip 29 is laterally deflectable 180° to one side of the longitudinal axis of the endoscope shaft 6, 24.

The following description of the flexible tip portion 29 will refer to both the endoscope with the step-tapered shaft and the endoscope with the uniformly tapered shaft 24, unless otherwise indicated. All of the embodiments can be equipped with the flexible tip 29, and the usage of the tip portion 29 will be substantially the same for all cases, but only the step-tapered and the uniformly tapered endoscope designs are used for illustration.

The flexible tip 29 has an outer diameter no larger than the distal portion of the semi-rigid shaft 6, 24 and has a length of about 8 cm. Depending on the subject, the flexible tip end 29 may reach all the way into the kidney 13 upon the distal end of the shaft 6, 24 being inserted into the subjects ureter 11.

Flexible tip 29 comprises a plastic outer tubing (i.e., polyurethane) which houses the working channels of the endoscope. As shown in FIGS. 6 and 7, outer opposite sides of the tip end 29 have a series of lateral notches 59 cut into the sides to enable lateral deflection as is known in the art. One of the series of notches 59 lies across the side of tip end 29 toward which tip end 29 deflects. The cross section provided by FIG. 8 shows two stainless steel spring guide wires 42, 43 within the plastic tubing which are attached, one each to the notched sides of tip 29. The spring guide wires 42, 43 lead through main shaft 6, 24 to control 51 at handle 12 as shown in FIGS. 6 and 7. When the user moves the control 51 in one direction, one spring guide wire 43 (42) is placed under tension and pulls tip end 29 to the side to which that spring guide wire is attached. When the user moves control 51 in an opposite direction, the second spring guide wire 42 (43) placed under tension and the other spring guide wire 42 (43) is released. Flexible tip 29 then straightens to the side to which the second spring guide wire 42 (43), now tensioned, is attached.

By rotating handle 12 180°, the flexible tip 29 is brought to an opposite portion of the plane in which it was being flexed. Note that such rotation is made possible by the rigidity of main tube portion 23, 24. The flexible tip 29 can then be flexed 180° to one side in this portion of a plane by control 51 in a manner similar to that previously described. In this fashion, flexible tip 29 can be flexed through 360° and provide any necessary angle of view.

Other means for flexing the tip end 29 may be used. In the above-described method, additional wires may be connected to other sides of the flexible tip end and the tip end may have notches along those other sides to provide lateral flexing in more than two directions.

In another design of control 51 for laterally flexing tip end 29, a lock and release scheme may be employed. In such a scheme, control 51 may be locked in place once the user has positioned it to provide a desired angle of deflection of tip end 29. In order to subsequently change the position of control 51, and thus the angle of deflection of tip end 29, control 51 must be unlocked or released. Thus, this scheme provides stabilization of control 51 and flexible tip end 29 once control 51 is positioned as desired.

The cross section of FIG. 8 shows the inside of an endoscope shaft which has a controllable flexible tip. Both the step-tapered and uniformly tapered endoscopes of FIGS. 6 and 7 have this layout of working channels. The layout is similar to that of the endoscopes shown in FIGS. 2 and 3 without the flexible tip portion 29, but with the addition of the spring guide wires 42, 43 which control the flexible tip. Hence, image carrying channel 44 corresponds to bore opening 39 of the handle, and working channels 46, 48 correspond to bore openings 53 and 57 of the handle. Outer casing 59 and fiber optics 55 correspond to outer casing 49 and fiber optics 45 respectively, as described above.

It is understood that other materials and dimensions may be used for the endoscopes of the present invention keeping in mind the dimensions of the affected body parts. Further, the number and dimensions of the channels employed are variable depending on the accessories (i.e., dye laser, fiber optics, etc.) used in conjunction with the endoscope. Alternatively, other shaped handles and handles of other designs may be used.

While the invention has been particularly shown and described with reference to embodiments thereof, it will be understood by those skilled in the art that various changes in form and details may be made therein without departing from the spirit and scope of the invention as defined by the appended claims.

One particular variation of the present invention involves the cross sectional shape of the endoscope shaft. Although shown in the preferred embodiments having a substantially circular cross section, the shaft may also have an elliptical cross section or one which is somewhat triangular. Other shapes are also possible, provided that there is some change in cross sectional diameter between the proximal and distal ends of the endoscope. In fact, different regions of the same shaft may have a different cross sectional shape as well as different diameter characteristics.

We claim:

1. A rigid endoscope comprising:
a rigid shaft which is sufficiently rigid such that it is displaced through axial and rotational translation by maneuvering one end of the shaft, the rigid shaft having at least three stages of different outside diameters, the stages being in order of outside diameter with a smaller diameter stage being at a distal end of the shaft and a step between the first and second stages positioned in the distal third of the rigid shaft to enter and dilate a ureter.

2. An endoscope as claimed in claim 1 wherein the length of the shaft is about 37-44 cm.

3. An endoscope as claimed in claim 1 wherein the shaft has a rigidity such that a minimum normal force of 250 grams applied at the distal end causes the distal end to deflect about 5 cm in a direction normal to a major axis of the shaft.

4. An endoscope as claimed in claim 1 further comprising:
a tip portion coupled to the distal end of the shaft, the tip portion being flexible relative to the endoscope shaft; and
means for laterally moving the tip portion relative to the shaft.

5. An endoscope as claimed in claim 1 wherein the distal end of the shaft has a circular cross-section of an outer diameter of less than 3 mm.

6. An endoscope as claimed in claim 1 wherein the shaft is multichanneled, one channel for viewing through from one end to objects outside the distal end, a second channel for carrying laser radiation to objects outside the distal end of the endoscope.

7. An endoscope as claimed in claim 6 further comprising illuminating light means positioned within the endoscope for delivering illuminating light to the distal end.

8. An endoscope as claimed in claim 6 wherein other channels are used for passing fluids.

9. An endoscope as claimed in claim 1 wherein the distal end of the endoscope is filled with epoxy which is ground to a smooth curved outer surface.

10. An endoscope as claimed in claim 1 wherein one of said stages of the endoscope shaft has an outside diameter which decreases toward the distal end of the shaft.

11. An endoscope as claimed in claim 1 wherein the shaft has three of said stages of different outer diameters.

12. An endoscope as claimed in claim 11 wherein the stage of smallest outer diameter is about 12-13 cm in length.

13. An endoscope as claimed in claim 1 wherein the stage of smallest outer diameter is about 12-13 cm in length.

14. An endoscope as claimed in claim 1 wherein the overall length of the shaft is about 20-25 cm.

15. An endoscope as claimed in claim 1 wherein each stage has rounded smooth ends for providing a gradual change in outer diameter between stages of the shaft.

16. An endoscope as claimed in claim 1 wherein each of said stages comprises an individual tube originating at the proximal end of the shaft and extending toward the distal end, the individual tubes of larger diameter enclosing part of a length of any individual tubes of smaller diameter.

17. An endoscope as claimed in claim 16 further comprising a smooth solder connection between each individual tube.

18. A method for performing an internal examination of a subject's body canal, the steps comprising:
providing a multi-channel rigid endoscope having a rigid shaft which is sufficiently rigid such that it is displaced through axial and rotational translation by maneuvering it from one end, the rigid endoscope shaft having a plurality of stages of different outside diameter, the stages being in order of outside diameter with steps between stages and with a smaller diameter stage being at a distal end of the shaft;
dilating a body canal with the small diameter of the distal end of the rigid endoscope shaft allowing the thicker portions of the endoscope shaft to penetrate said body canal; and
viewing said body canal through one channel in the endoscope from the proximal end.

19. A method as claimed in claim 18 wherein one of said stages of the endoscope shaft is tapered along its length such that its diameter decreases toward the distal end of the endoscope.

20. A method as claimed in claim 18 wherein each of the stages of the endoscope shaft comprises an individual tube originating at the proximal end of the shaft and extending toward the distal end, the individual tubes of larger diameter enclosing part of a length of any individual tubes of smaller diameter.

21. A method for breaking calculus in a body, the method comprising:
providing a multichanneled endoscope having a rigid shaft which is sufficiently rigid such that it is displaced through axial and rotational translation by maneuvering one end of the shaft, the rigid shaft having a plurality of stages of different outside diameter, the stages being in order of outside diameter with steps between stages and with a smaller diameter stage being at a distal end of the shaft;
dilating a body canal with the small diameter of the distal end of the endoscope shaft allowing the thicker portions of the shaft to penetrate said body canal;
positioning the distal end of the endoscope shaft adjacent to the calculus by maneuvering the proximal end of the endoscope; and
transferring laser radiation through a second channel in the endoscope from the proximal end to the calculus adjacent to the distal end.

22. A method as claimed in claim 21 wherein one of said stages is tapered along its length such that its outer diameter decreases toward the distal end of the endoscope.

23. A method as claimed in claim 21 wherein each of the stages of the endoscope shaft comprises an individual tube originating at the proximal end of the shaft and extending toward the distal end, the individual tubes of larger diameter enclosing part of a length of any individual tubes of smaller diameter.

24. A fiber optic endoscope comprising:
a shaft having an overall length of about 37-44 cm and three stages of different outside diameter, the stages being in order of outside diameter with a smaller diameter stage being at a distal end such that the endoscope shaft is less rigid in a region at the distal end relative to a region at a proximal end, the shaft being sufficiently rigid such that it is displaced through axial and rotational translation by maneuvering it from one end, and such that a minimum normal force of 250 grams applied to the distal end causes the distal end to deflect about 5 cm in a direction normal to an initial major axis of the shaft.

25. A fiber optic endoscope comprising:
a shaft having an overall length of about 37-44 cm and which is tapered along its length such that its outer diameter decreases uniformly toward its distal end, the shaft sufficiently rigid such that it is displaced through axial and rotational translation by maneuvering it from one end, and such that a minimum normal force of 250 grams applied at the distal end causes the distal end to deflect about 5 cm in a direction normal to a major axis of the endoscope shaft.

* * * * *